United States Patent [19]
Steinhauser et al.

[11] Patent Number: 5,505,218
[45] Date of Patent: Apr. 9, 1996

[54] DEVICE FOR CLEANING AND/OR DISINFECTING AND/OR MAINTAINING MEDICAL OR DENTAL INSTRUMENTS

[75] Inventors: Pius Steinhauser; Anton Bodenmiller, both of Leutkirch; Herbert Lott, Bad Wurzach, all of Germany

[73] Assignee: Kaltenbach & Voigt GmbH & Co., Biberach, Germany

[21] Appl. No.: 323,245

[22] Filed: Oct. 14, 1994

Related U.S. Application Data

[62] Division of Ser. No. 131,465, Oct. 4, 1993, Pat. No. 5,380,369.

[30] Foreign Application Priority Data

Oct. 22, 1992 [DE] Germany ............... 42 35 712.8

[51] Int. Cl.⁶ ....................................... B08B 3/12
[52] U.S. Cl. .............. 134/95.1; 134/102.1; 134/170; 134/184
[58] Field of Search ................ 134/1, 22.1, 42, 134/95.1, 95.2, 102.1, 102.2, 102.3, 169 R, 170, 184, 56 R, 57 R, 58 R; 422/20, 28

[56] References Cited

U.S. PATENT DOCUMENTS

| | | | |
|---|---|---|---|
| 4,193,818 | 3/1980 | Young et al. ............... | 134/102.1 X |
| 4,299,244 | 11/1981 | Hirai .......................... | 134/102.1 |
| 4,486,174 | 12/1984 | Eibofner et al. . | |
| 4,637,378 | 1/1987 | Sasa .......................... | 134/102.1 X |
| 4,703,767 | 11/1987 | Spitler et al. ............... | 134/102.1 |
| 4,892,112 | 1/1990 | Knetsch .................... | 134/102.1 |
| 5,197,499 | 3/1993 | Bodenmiller et al. ...... | 134/102.3 X |
| 5,279,799 | 1/1994 | Moser ....................... | 134/102.2 X |

FOREIGN PATENT DOCUMENTS

| | | | |
|---|---|---|---|
| 217766 | 5/1968 | U.S.S.R. ............... | 134/102.2 |
| 670295 | 6/1979 | U.S.S.R. ............... | 134/102.3 |

*Primary Examiner*—Philip R. Coe
*Attorney, Agent, or Firm*—Scully, Scott, Murphy & Presser

[57] ABSTRACT

In a process for cleaning and/or disinfecting and/or maintaining medical or dental instruments, in a washing container filled with liquid, particularly water, the at least one tool holder being washed internally and externally and additionally having ultrasound applied thereto, in the case of a hollow or sleeve-shaped instrument, particularly tool holder, the cavity of the instrument, in particular the cavity or cavities of the tool holder accommodating the mechanical drive elements, is drained and ultrasound is then applied to the tool holder.

12 Claims, 6 Drawing Sheets

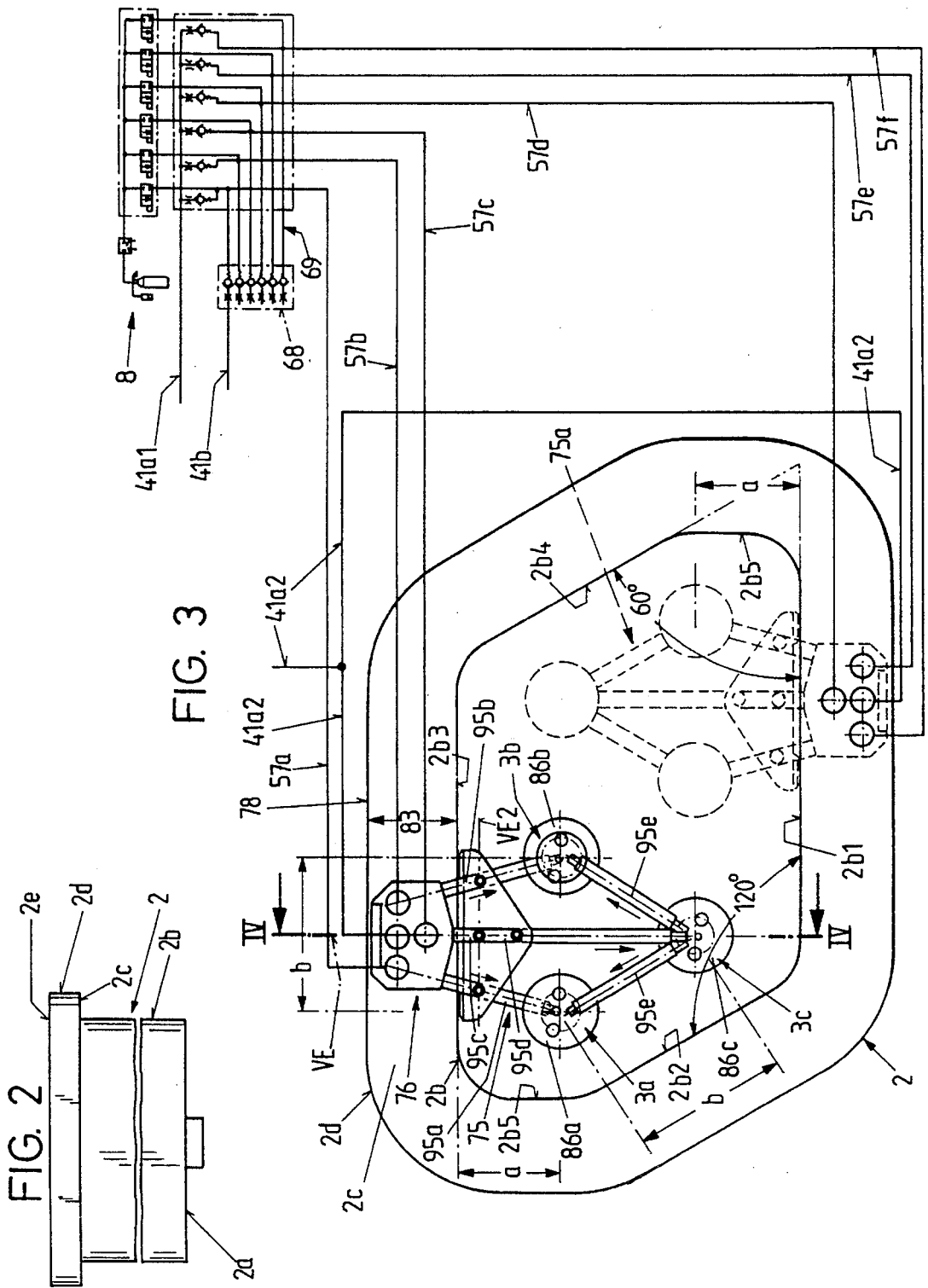

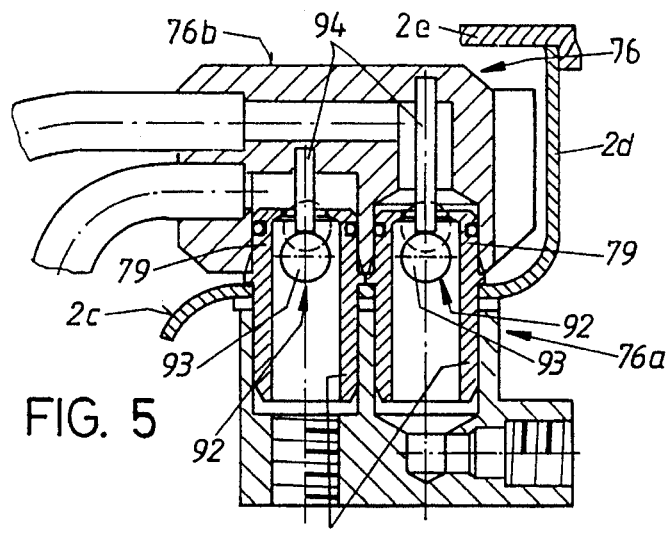
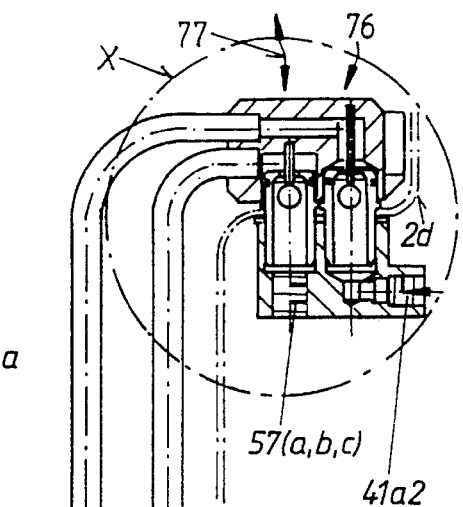
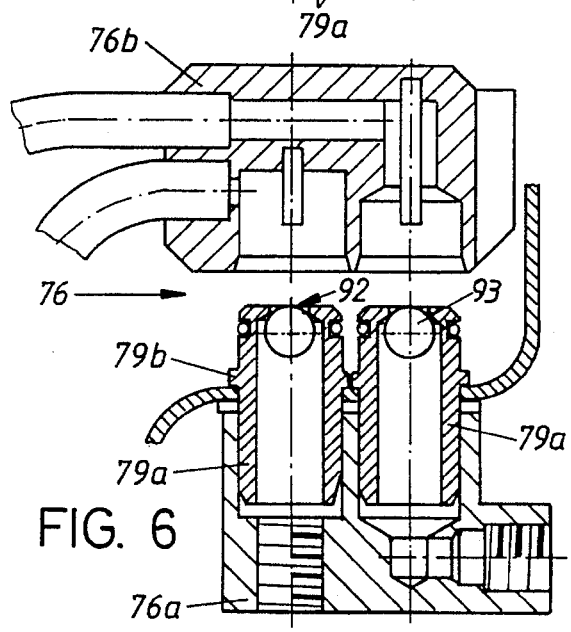
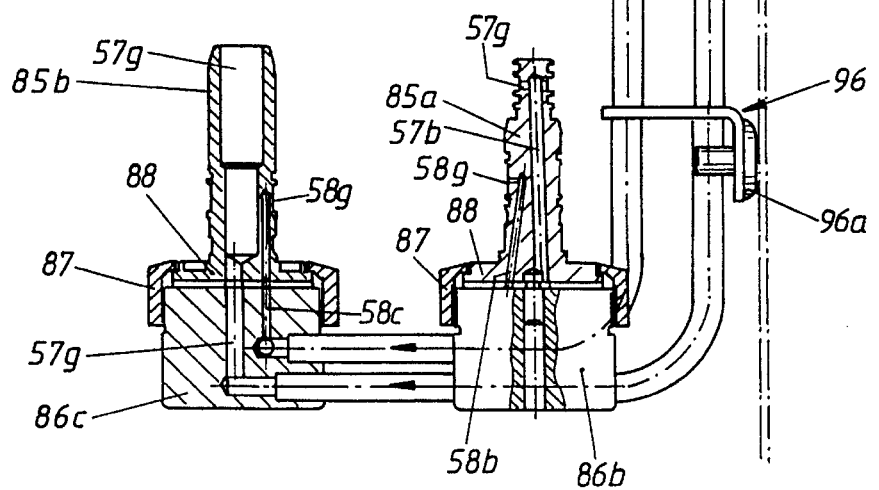
FIG. 5
FIG. 6
FIG. 4

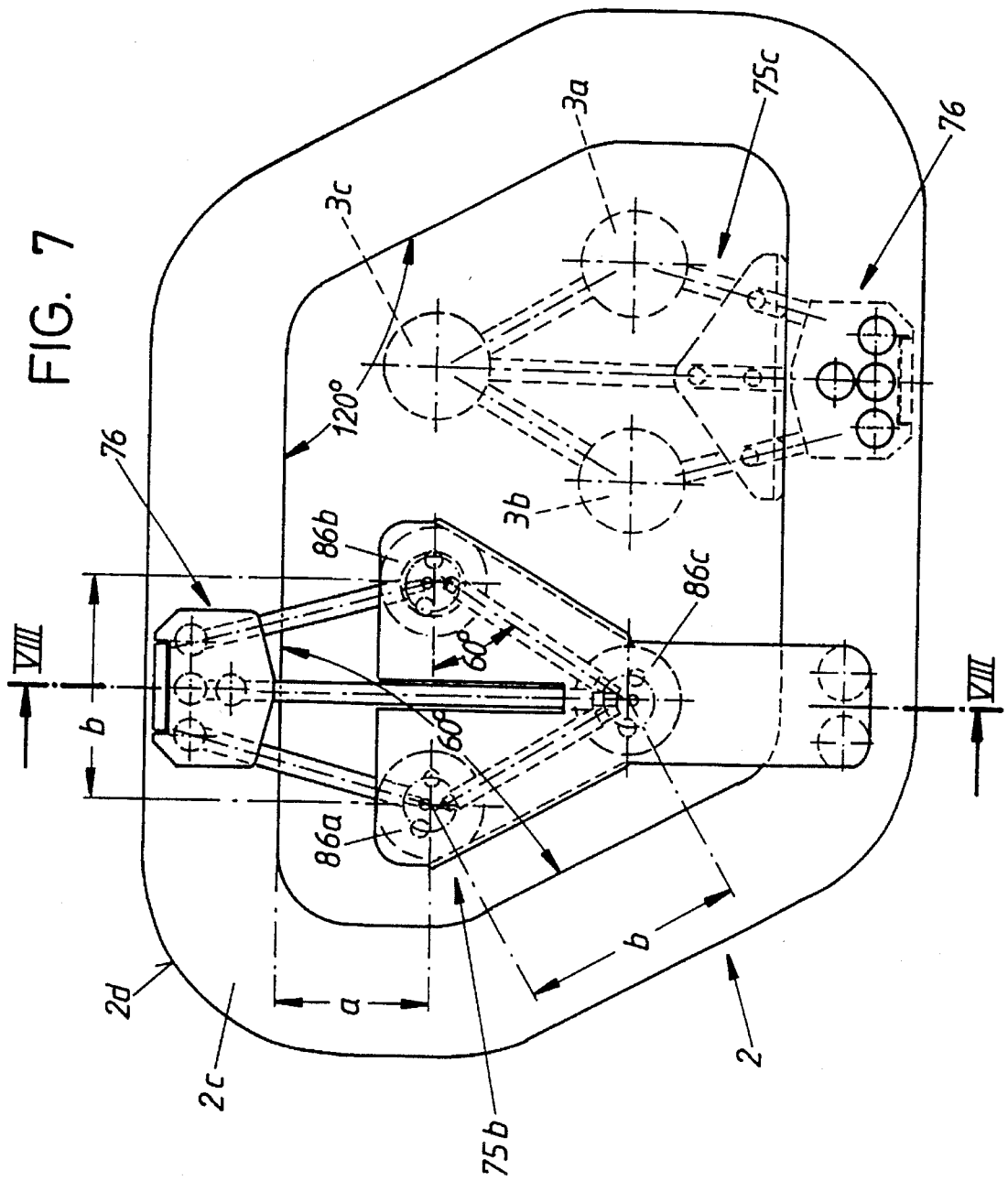

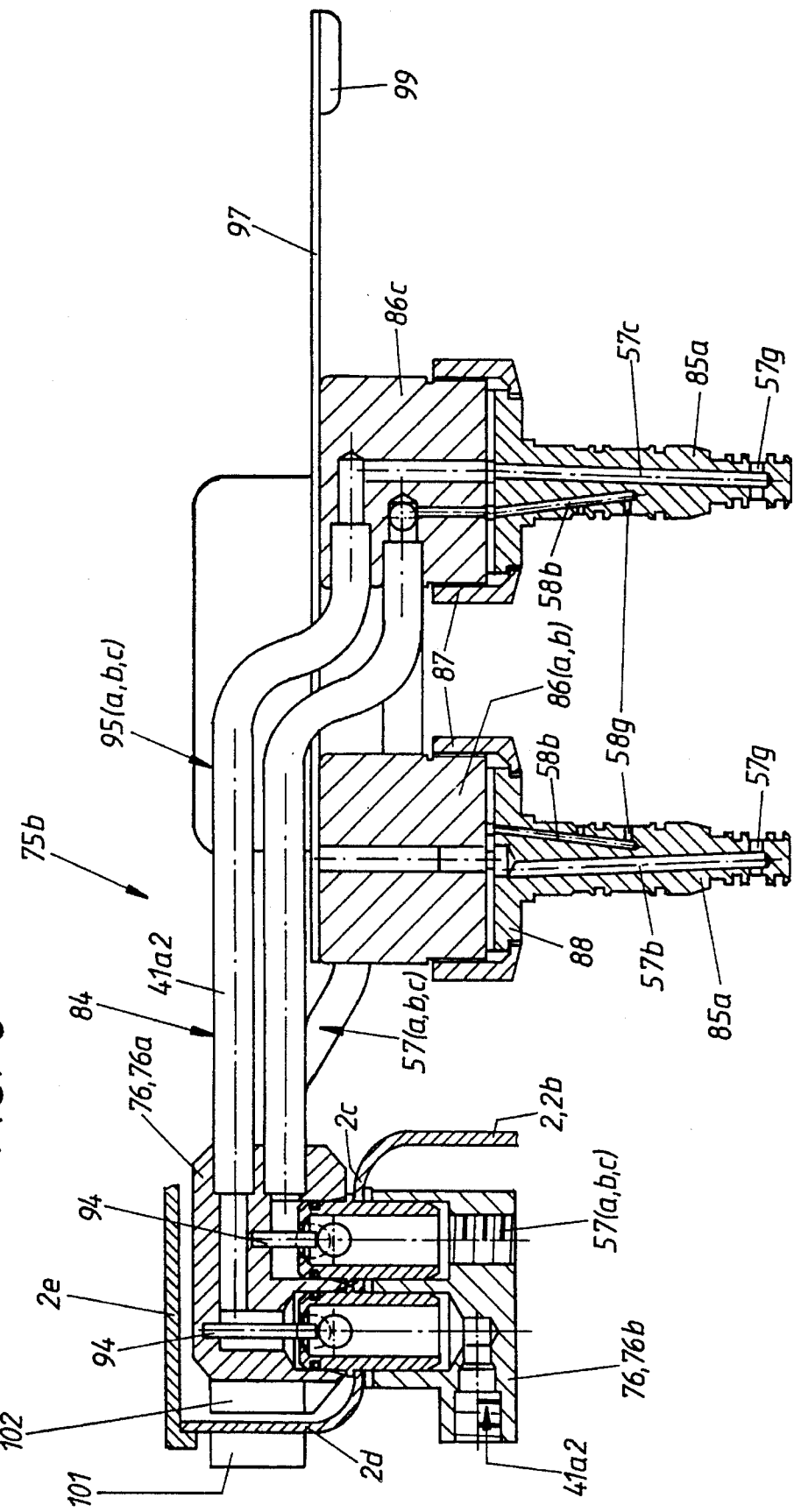

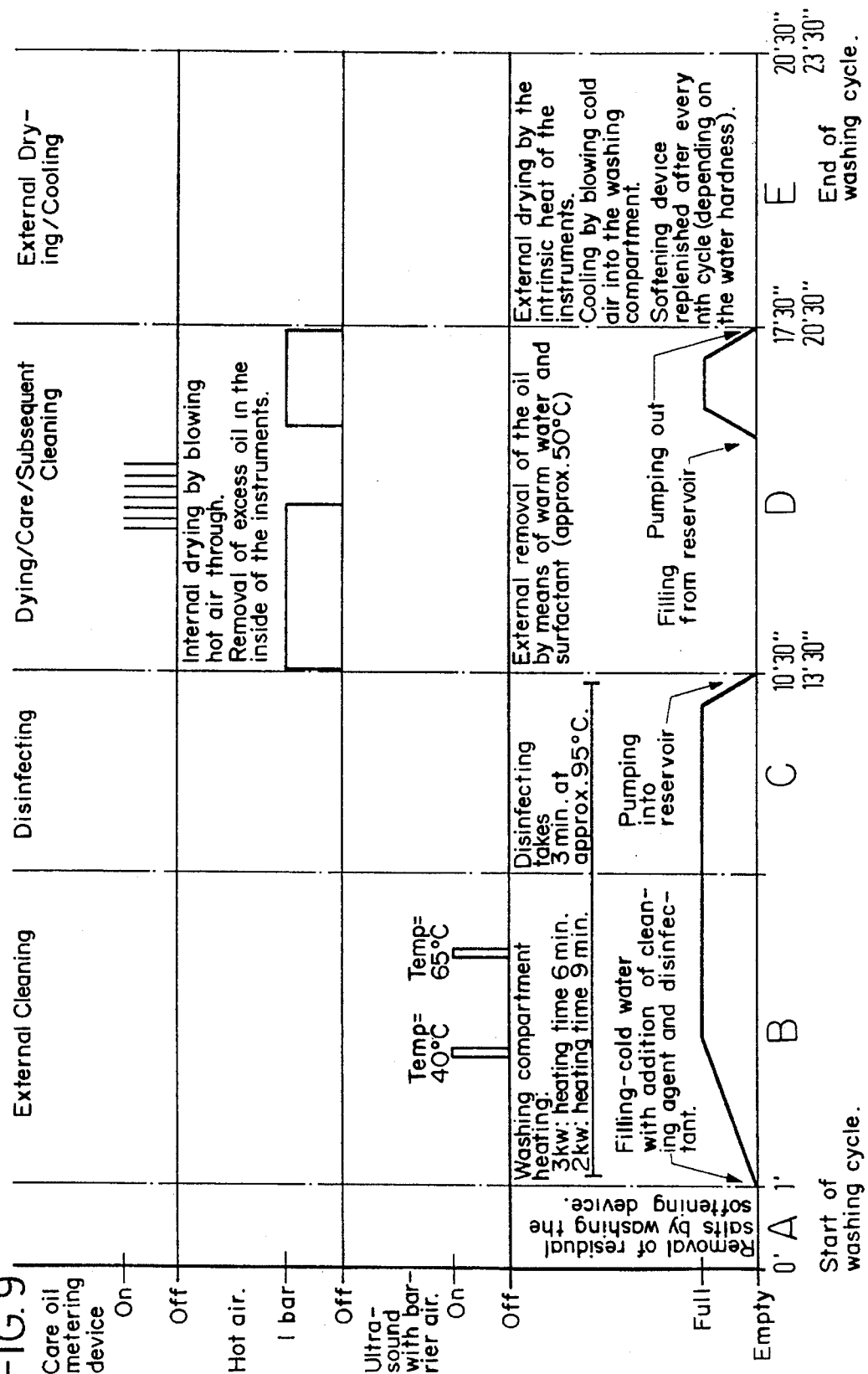

DEVICE FOR CLEANING AND/OR DISINFECTING AND/OR MAINTAINING MEDICAL OR DENTAL INSTRUMENTS

This is a divisional of application Ser. No. 08/131,465, filed on Oct. 4, 1993, and now U.S. Pat. No. 5,380,369.

TECHNICAL FIELD OF THE INVENTION

The invention relates to a device for cleaning and/or disinfecting and/or maintaining medical or dental instruments.

BACKGROUND OF THE INVENTION AND PRIOR ART

The tool holders under consideration are the tubular-form parts of treatment instruments which the doctor holds as a gripping sleeve in the course of treatment. At its front a tool holder under consideration carries a treatment tool, e.g. a drill, and with its rear end it can be coupled by means of a plug-in/rotary coupling to a so-called supply part to which energy to power the treatment tool and also treatment media in associated fluid lines can be supplied through a supply cable. Both the drive energy line and the fluid lines pass through the plug-in/rotary coupling and continue in the tool holder. The fluid lines are usually air, water or spray lines which extend in the form of conduits or hoses as far as the front end of the tool holder and emerge there in order to be able to brought to bear at the treatment point, and/or as far as an air turbine arranged in the tool holder. An energy line can be an electrical line, a fluid line, particularly an air line, or also a mechanical connection, e.g. in the form of a spindle which transmits a torque. There are treatment instruments in which the drive motor is arranged in the supply part or the tool holder. For structural reasons the designs that have proved successful in practice are those in which an electric motor is arranged in the supply part and an air motor (in the case of a so-called turbine) in the tool holder. The drive connection between the drive motor and the treatment tool is made by means of mechanical couplings, gear trains and gear drives. A tool holder under consideration may be either a straight sleeve-like component or a so-called angled or elbow piece. In most cases, currently common plug-in/rotary couplings between the tool holder and the supply part are formed by a round plug-in stud arranged on the supply part and projecting therefrom and a plug-in hole arranged at the rear end of the tool holder and accommodating the plug-in stud. A tool holder of this kind therefore comprises mechanical, pneumatic and/or hydraulic functional elements.

When a tool holder is used to treat the human or animal body or to work on prostheses which are worn by patients, pollution and contamination by pathogens is unavoidable. It is thus necessary to clean and disinfect a tool holder after use. In view of the mechanical functional parts it is also necessary in this case to maintain the mechanics, e.g. with a special maintenance oil, in order to ensure uninterrupted operation and a long service life for the mechanical drive components.

A device which makes this possible is disclosed in DE-40 24 171 A1. In this known arrangement, the cleaning, disinfecting and maintenance of at least one, preferably several tool holders takes place simultaneously, in a water bath in a container, a mounting in the container being associated with each tool holder, with which the associated tool holder can be mounted in an upright position. A compressed air line which terminates in the inside of the associated tool holder is associated with each mounting. The compressed air that can be supplied via the compressed air line can be optionally heated so that hot compressed air can be blown through the tool holder. An oil supply with an oil doser is also connected to the compressed air line via a line section so that oil can be optionally introduced into the cavity of the tool holder which accommodates the mechanical drive parts. In this known arrangement the cleaning and disinfecting of the tool holder externally and internally takes place by boiling in the water bath, with the possibility of adding cleaning agents and surfactants to the water bath. Internal cleaning and maintenance also takes place by means of hot compressed air and oil. For each tool holder treatment procedure the container provided is filled with hot water or heated. The liquor is pumped away after the treatment.

OBJECT OF THE INVENTION

The object of the invention is to improve and/or intensify the cleaning and/or disinfecting in the case of a device of the kind as described herein.

SUMMARY OF THE INVENTION

According to the invention there is provided a device for cleaning and/or disinfecting and/or maintaining medical or dental instruments in a washing container filled with liquid, particularly water, the at least one tool holder being washed internally and externally and additionally having ultrasound applied thereto,
wherein
in the case of a hollow or sleeve-shaped instrument, particularly tool holder, the cavity of the instrument, in particular the cavity or cavities of the tool holder accommodating the mechanical drive elements, is drained and ultrasound is then applied to the tool holder.

In the device according to the invention the sound waves of an ultrasonic cleaning device are additionally applied to the tool holder, thereby intensifying and improving both the cleaning and the disinfecting. The ultrasonic cleaning only takes place when a cavity or the cavities accommodating the mechanical drive parts of the instrument have been drained. This drainage takes place by blowing through these cavities by means of compressed air. The ultrasonic cleaning is then switched on. This prevents gravitational and cavitation damage in the cavities of the tool holder which arises if ultrasonic cleaning takes place when a liquid is present in these cavities.

According to the invention there is also provided a device for carrying out the inventive treating sequence with a washing container in which the instrument is held by means of a carrier and with an ultrasonic cleaning device which can be switched on and off by a control device,
wherein
a carrier fixing the instrument is provided,
wherein a supply line for a gaseous medium under pressure, particularly compressed air, which terminates directly in the cavity of the instrument, particularly in the cavity or cavities of the instrument accommodating the mechanical drive elements, is associated with the carrier,
and wherein
the supply of the medium can be optionally switched on and off by means of a control device.

The device according to the invention is distinguished by a simple and compact construction which is economic to manufacture and can also be advantageously integrated and is also reliable in operation.

Embodiments of the invention may contain features which further contribute towards a solution of the problem, improve the construction and also improve the efficiency or utilization of the ultrasonic energy.

BRIEF DESCRIPTION OF THE DRAWINGS

The invention and further advantages which can be achieved with it will be described in greater detail below with reference to preferred embodiments and the drawings, in which:

FIG. 2 shows a side view of a container of the device;

FIG. 3 shows a schematic enlarged top view of the container with carrier units for the tool holders;

FIG. 4 shows the partial section IV—IV in FIG. 3;

FIG. 5 shows an enlarged view of the plug-in connection marked X in FIG. 4;

FIG. 6 shows the plug-in connection in the open position;

FIG. 7 shows a top view of the container with carrier units of modified design;

FIG. 8 shows the partial section VIII—VIII in FIG. 7;

FIG. 9 shows a functional diagram of the device.

DETAILED DESCRIPTION OF PREFERRED EMBODIMENTS ACCORDING TO THE INVENTION

Figure 1:
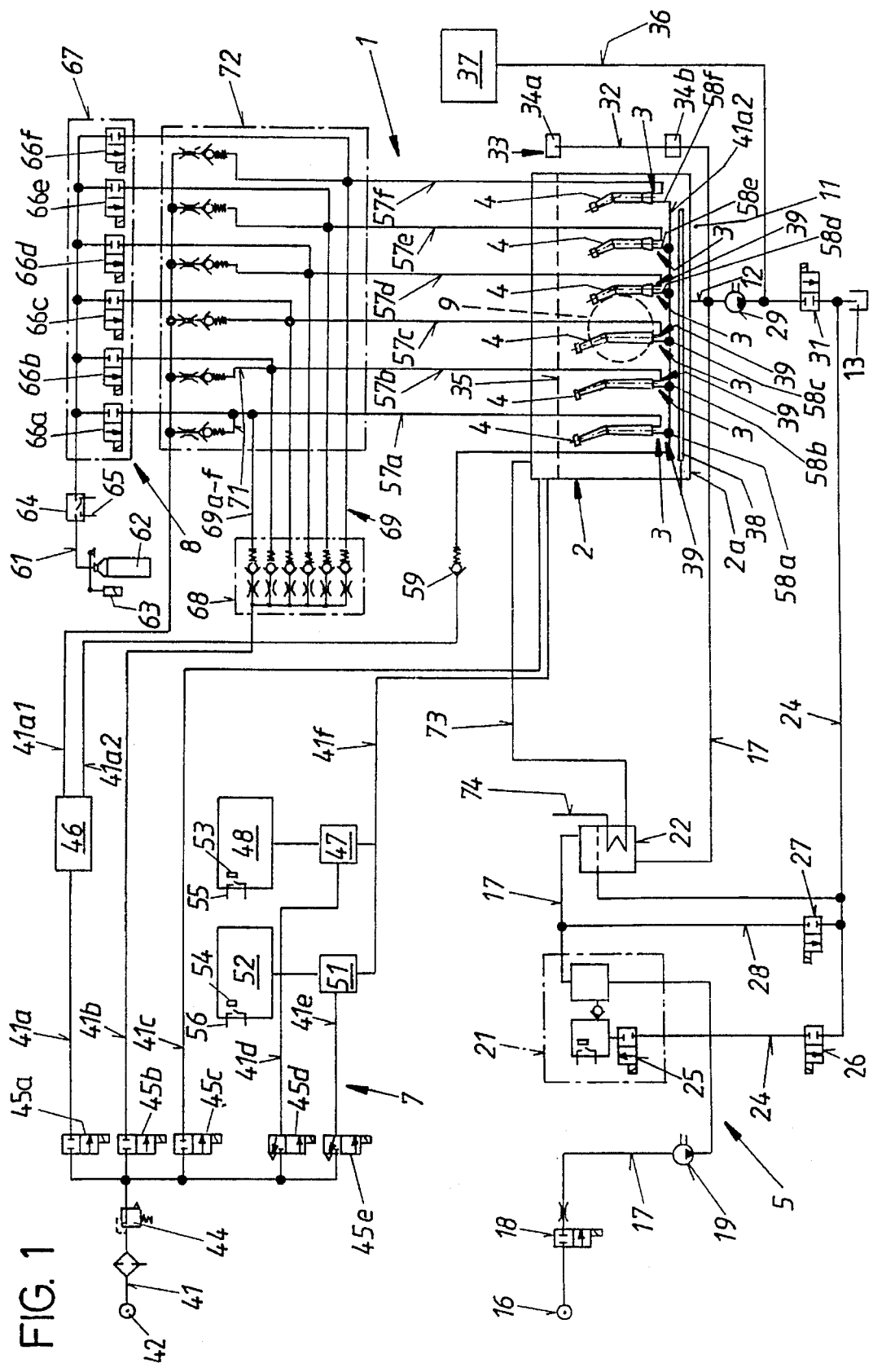
FIG. 1 shows a schematic representation of a device according to the invention for cleaning, disinfecting and/or maintaining tool holders, in the form of a maintenance station.

The main components of the device 1 are a pot-shaped washing container 2 with a multiplicity of mountings 3 in the interior of the container 2 each for one tool holder 4, in this embodiment six mountings 3, a water supply system 5, with which water can be supplied to the washing container 2 and can also be lead from it, a compressed air supply system 7, a care agent supply system 8 and an ultrasonic cleaning device, of which only one ultrasonic transducer 9 for applying ultrasound to the washing container 2 is illustrated.

In the region of its base 11 the washing container 2 has a supply and discharge line 12, which is part of the water supply system 5, and with a water outlet 13. The following are arranged downstream of each other in the direction of flow, in the water supply line 17 which can be connected to a water connection 16: a first solenoid valve 18, a pump 19, particularly for pressure boosting purposes, a softening device 21 and a condenser 22. The softening device 21 is connected directly to the water outlet 13 by means of a discharge line 24 in which one or two solenoid valves 25, 26 are arranged one behind the other, so that the waste water can be directly discharged into the water outlet 13 in order that the-softening device can be washed and regenerated. A fourth solenoid valve 27 is arranged in a line section 28 connecting the water supply line 17 behind the softening device 21 and the discharge line 24 behind the solenoid valve 26. A second pump 29 and a fifth solenoid valve 31 are arranged behind each other in the supply and discharge line 12 in the direction of the water outlet 13. The water supply line 17 is connected to the supply and discharge line 12 between the washing container 2 and the second pump 29, a further line section 32 which leads to a water level display device or measuring device 33 with a level switch 34a, 34b also being in this area. The maximum water filling level in the washing container 2 is denoted by 35. It is above the tool holders 4 placed in or on the mountings 3. A further branch line 36 which leads to an intermediate reservoir 37 arranged above the washing container 2 branches off between the second pump 29 and the solenoid valve 31. An electric heating device 38 with at least one electric heating element is arranged in the bottom of the washing container 2.

Each mounting 3 preferably has a round coupling stud onto which the associated tool holder 4 can be optionally placed, or from which it can be removed, with a correspondingly round coupling recess. This forms a plug-in/rotary connection 39 of the kind known for the rotatable connection of tool holders 4 with associated supply parts (not shown).

The compressed air supply system 7 has five compressed air lines 41a to 41e connected in parallel, which start from a common compressed air supply line 41 which can be connected to a compressed air supply 42 and in which an air filter and a pressure control valve 44 are arranged. A solenoid valve 45a–45e is arranged in each compressed air line 41a–41e. A preferably electrically powered air heater 46, in which or behind which the compressed air line 41a branches into two compressed air line branches 41a1 and 41a2, is also arranged in the compressed air line 41a. The compressed air line 41c terminates in the washing container 2 above the maximum water level 35. A cleaning agent metering device 47, which is connected to a cleaning agent container 48 directly or via a line section, is arranged in the compressed air line 41d. A surfactant metering device 51, which is connected to a surfactant reservoir 52 directly or via a line section, is arranged in the compressed air line 41e. Both reservoirs 48, 52 have a level meter 53, 54 and an electric switch 55, 56. Behind the metering devices 47, 51 the compressed air lines 41d and 41e come together to form a common compressed air line 41f which also terminates in the washing container 2 above the maximum water level 35.

Two supply lines, viz. a first supply line 57a–57f and a second supply line 58a–58f are associated with each mounting 3. The supply lines 58a–58f are connected to the common supply line branch 41a2 in which a non-return valve 59 opening in the direction of flow is arranged. The first supply lines 57a–57f are connected to a common care agent supply line 61 which starts from a pressurized care agent container 62, e.g. a spray bottle, an electrically controllable valve 63 being provided with which the output of the care agent into the supply line 61 can be optionally controlled by opening and closing. A measuring or monitoring device 64 with an electric switch 65 is also arranged in the supply line 61. Solenoid valves 66a to 66f which are combined in a care agent distributor 67, e.g. in the form of a valve block, are arranged in the first supply lines 57a–57f.

In a compressed air distributor 68 the compressed air line 41b branches into the number of compressed air line branches 69a–69f corresponding to the number of mountings 3, in each of which branches a throttle and a non-return valve opening in the direction of flow are arranged and each of which is connected to one of the first supply lines 57a–57f. The first supply lines 57a–57f are also each connected to the compressed air line branch 41a1 by means of a line section 71, a throttle and a non-return valve opening in the direction of flow also being arranged in the line section 71 in each case. The above-mentioned line connections are associated with a compressed air distributor 72.

From the region above the maximum water level 35 a steam line 73 extends from the washing container 2 to the condenser 22 in which steam flowing from the washing container 2 condenses and is returned to the water supply system 5. The steam line 73 ends in the area of the condenser 22 as a free outgoing air line 74.

As can be seen from FIGS. 3 to 7, several, here in each case three mountings 3 are combined to form a tool holder carrier unit 75 which is detachably connected to the washing container 2 in a plug-in socket 76, the associated supply lines 57a–57f and 41a2 passing through the plug-in socket 76 in a leakproof manner. Different mountings 3 adapted to given tool holder designs can be fitted and/or removed quickly and easily in this way. The device 1 can thus be simply and quickly converted to tool holders 3 of different coupling sizes and shapes by fitting available matching carrier units 75.

The plug-in socket 76 is preferably arranged on the upper edge of the washing container 2, offset to the outside. In this position a vertical insertion direction (arrow 77) can be advantageously achieved so that when the carrier unit 75 is inserted into the washing container 2 the plug-in socket 76 can be connected in a space-saving manner. The plug-in socket 76 comprises a plug-in socket part 76a fixed to the washing container 2 and a plug-in socket part 76b fixed to the carrier unit 75. The plug-in socket part 76a can comprise two parts which are arranged on either side of the container wall 2b of the washing container 2, one part, the inner part in this case, passing through the container wall 2b in a suitable hole and resting on the inner hole edge with a shoulder, whilst the other part, in this case the outer part, is placed on the first part like a sleeve from the other side of the container wall 2b and is thus connected with it, e.g. detachably by means of a thread, or captively e.g. by means of welding or soldering.

The upper edge area of the washing container 2 is preferably widened with a horizontal flange wall 2c, extending from the container wall 2b, which is adjoined by an approximately vertical edge wall 2d in the upwards direction. The lateral widening is larger in size than the plug-in socket part 76a so that this part can be arranged in the area of the edge widening 83 formed in this way and can pass through the flange wall 2c. 2e denotes a cover which rests on the edge wall 2d and thus covers the carrier unit 75.

The upper part of the plug-in socket part 76a projects upwards in a stud-like manner and thus forms one or more studs 79, preferably as many as there are supply lines 57a–57c and 41a2 passing through the plug-in socket 76, onto which studs the plug-in socket part 76b associated with the carrier unit 75 can be inserted with one or more plug-in recesses of corresponding number and corresponding shape and size in a closing manner. The studs 79 are preferably formed by sleeves 79a, each having a shoulder 79b, which are inserted and fixed in the plug-in socket part 76a.

The plug-in socket part 76b associated with the carrier unit 75 is connected by means of a preferably Z-shaped shaft 84 with several, in this case three, mountings 3 which are arranged in the corners of an imaginary triangle, two of the mountings 3a, 3b adjacent to the container wall 2b being arranged symmetrical to a vertical plane VE extending at right angles to the peripheral wall 78 and an associated further mounting 3c being displaced in the direction of the side facing away from the associated plug-in socket part 76b, whereby the mountings 3a, 3b, 3c are arranged at the corner points of an imaginary equilateral triangle.

As already stated the mountings 3 are formed by round plug-in studs 85 which in the upright arrangement of the tool holders 4 in the embodiment according to FIGS. 1 to 5 extend upwards from a carrier base part 86a, 86b, 86c associated with each mounting 3 and are preferably detachably fixed. A coupling ring 87 which overlaps a base flange 88 of the associated plug-in stud 85 and is screwed onto the associated, preferably round carrier base part 86, can be used for this. Associated with the plug-in/rotary coupling 39 are latching elements which provide a detachable latching of the tool holders 4 in the inserted position, as is common for a quick-action coupling for tool holders.

In practice, plug-in/rotary couplings 39 with plug-in studs 85 of differing shape and/or size are usually made for treatment instruments air-powered by means of an air motor and for treatment instruments electrically powered by means of an electric motor. In this embodiment the plug-in studs denoted by 85a are designed for a tool holder 4 powered by compressed air, the plug-in stud 85b being designed for an electrically powered tool holder 4.

The compressed air line 41a2 is connected to the plug-in socket part 76a and extends through the plug-in socket 76 and the shaft 84 as far as the carrier base parts 86a, 86b, 86c. This is where the associated second supply line 58a to 58c branches off and extends as an axis-parallel conduit through the associated plug-in stud 85 from which it terminates radially in an outlet opening 58g, preferably in a peripheral groove and between two ring seals, as is known per se for plug-in/rotary couplings.

The first supply lines 57a–57c are also connected to the plug-in socket part 76a associated with the washing container 2 and they extend further as separate supply conduits 57g in the carrier part 75, extending coaxially in the area of the associated plug-in stud 85 and emerging from the associated plug-in stud 85 at outlet openings 57h, axially offset from the outlet openings 58g, coaxially in the case of a plug-in stud 85b for a tool holder powered by an electric motor and radially in a peripheral groove between two sealing rings in the case of a plug-in stud 85a for a so-called turbine tool holder. Fluid conduits or the cavities which accommodate the mechanical gearing, e.g. a drive spindle, are continued in the associated tool holder 4 opposite the outlet openings 57g, 58g of the supply conduits 57a–57c.

A stop valve 92, whose purpose is to close the associated conduit if no carrier unit 75 is fitted, is provided in the plug-in socket part 76a in each first supply conduit 57a–57c and in the compressed air line 41a2. Each of these stop valves 92 is formed by a valve ball 93 in an enlarged conduit section in the plug-in socket part 76a, upstream of which a valve seat surrounding a valve opening is arranged in the direction of flow. If no carrier unit 75 is present the valve balls 93 close the stop valves 92 on the basis of an available pneumatic closing pressure, it being possible for compression springs pressing the valve balls 93 against the associated valve seat to be present. When a carrier unit 75 is fitted the valve balls 93 are maintained in the pressed open condition by means of pins 94 which are fixed coaxially with respect to the stop valve 92 in the plug-in socket part 76b and are of a length such that they pass through the valve opening whilst maintaining a circular gap and raise the valve balls 93 from the valve seats. For sealing purposes the stud or studs 79 are sealed by means of ring seals which surround them.

In this embodiment the shaft 84 of the carrier unit 75 comprises four thin pipes 95a–95d, preferably of metal, forming the supply line conduits 57a–57c and the compressed air line 41a2, which extend z-shaped between the plug in socket part 76b and the three carrier base parts 86 and are thus preferably laterally tightly connected, e.g. by bonding or soldering. The vertical sections of the pipes 95a–95c forming the supply lines 57a–57c extend in a vertical plane VE2 running at right angles to the vertical plane VE in the vicinity of the container wall 2b and they are each bent towards the associated carrier base part 86. The pipe 95d forming the compressed air line 41a2 extends to the carrier base part 86c in the vertical plane VE approximately parallel to the central pipe 95b. From this point the compressed air line 41a2 is connected to the carrier base parts 86a, 86b by means of two horizontal pipe sections 95e arranged in a V-shape. A stable design is achieved by arranging the pipes 95 in several planes.

Externally in the lower region of the pipes 95 there is arranged a preferably angular support part 96 which not only connects the pipes 95a, 95b, 95c to each other and thus stabilizes them, but also assures lateral support on the inner wall of the washing container 2. The outer vertical leg of the support part 96 preferably has one continuous buffer part, or two buffer parts at a distance from one another, 96a, of soft material which provide a soft support in on the peripheral wall 2b.

A further carrier unit 75a of the same design but in a position rotated horizontally through 180° is provided, this carrier unit 75a resting on the opposite edge flange 2c, with the plug-in socket part 76b in that plug-in socket 76, in a position displaced with respect to the carrier unit 75 perpendicularly to the vertical plane VE. Because of the rotated arrangement of the carrier units 75, 75a the six mountings 3 and/or carrier base parts 86 that are present adopt the shape of a parallelogram. The horizontal cross-sectional shape of the washing container 2 is preferably adapted to this shape and is thus parallelogram shaped, the corners of this parallelogram shape preferably being rounded.

The first supply lines 57d–57f and a branch line of the compressed air line branch 41a2 extend to the carrier unit 75a in corresponding manner.

In this embodiment flat and vertical container side walls 2b1 to 2b4 which define an inner corner in each case include an angle of approx. 60° or approx. 120°. In the region of each acute inner corner the initial part a of the container side walls 2b2, 2b4 which extend obliquely with respect to the carrier unit 75 or confront the vertical plane VE can be arranged parallel to the latter. These container side walls are designated as 2b5 in each case. The width a of these container side walls 2b2, 2b4 approximately corresponds to the distance between the mountings 3a, 3b and the container side wall 2b3.

An advantage of the oblique-angled and/or parallelogram-shaped cross-sectional area of the washing container 2 lies in the fact that it makes good use of space and/or is adapted to the carrier units 75, 75a so that the inserted tool holders 4 are thoroughly washed despite the fact that as little washing water as possible is used.

The fact that this shape improves the efficiency of the ultrasonic cleaning is a further advantage. The oblique-angled and/or parallelogram shape largely prevents those reflected sound waves, generated by reflection at the container wall 2b of the washing container 2, which are directly opposed to each other and would thereby impair their efficiency. As can be seen in particular from FIG. 3, the mountings 3 and the inserted tool holders 4 face the opposing container wall 2b with their entire surface and thus the ultrasonic waves coming therefrom can be effectively applied to them without substantial wave shadow formation and without substantial loss of performance. Any damaging resonance vibrations, oscillation couplings or oscillation initiation from the outside into the interior of the tool holder are largely prevented. In this embodiment the ultrasonic transducer 9 is fixed half way up the washing container 2 and in the central area of a side surface on the outside of the container wall 2b, e.g. by bonding.

The embodiment according to FIGS. 7 and 8, in which identical or comparable parts have the same reference numbers, differs from the above-described embodiment solely in that instead of an upright arrangement for the tool holders 4, a suspended arrangement is provided, i.e. the carrier base parts 86 with the plug-in studs 85 are in a position rotated through 180° in the upper area of the washing container 2, the plug-in studs 85 pointing downwards and the tool holders 4 being inserted suspended from underneath. To stabilize this arrangement a horizontal support arm 97 is provided, which extends from the carrier base part 86c most distant from the plug-in socket part 76b to the opposite edge of the washing container 2 and rests on the opposite edge flange 2d with a damper part 99 of soft material fixed on its underside. In this embodiment the shaft 84 and the pipes 95a–95c extend substantially horizontally. Otherwise this carrier unit 75b, and correspondingly formed but rotated further carrier unit 75c, are formed and/or arranged correspondingly to the carrier unit 75 and/or 75a.

The above-described solenoid valves are preferably 2/2-way valves which close the passage of the associated line in one switching position and open it in the other switching position.

The function of the device 1 will be described in greater detail below with the aid of FIG. 9, on whose abscissae the time and treatment steps A–E are plotted and on whose ordinates time stages are plotted.

A washing of softening device 21 is only activated in Treatment step A if the resin in the softening device 21 was regenerated with brine at the end of the previous care cycle. In this case the brine which remains in the resin container until the start of a new care cycle is washed out with fresh water.

Before a care cycle the tool holders 4 to be maintained are assigned to the associated mountings 3 by attaching them. The care cycle, which can proceed semi- or even fully automatically by means of an electrical control device (not shown) which is connected to the associated functional elements by means of signal and control lines, is then initiated. First of all the washing container 2 is filled with water by opening the solenoid valve 18 with an associated throughflow quantity limiter. Once a minimum level has been reached, e.g. when the electric heating device 38 is covered with water, the level switch 34 emits a signal to switch on the heating device 38. The cleaning agent is metered by opening the solenoid valve 45d for a specific period of time. The metered quantity of cleaning agent is forced into the washing container 2 through line 41f by means of compressed air. The washing water flows through the circular gap between the plug-in studs 85 and the instruments and/or tool holders 4 and into their interiors (media conduits, cavities for the tool drive) if there are no sealing rings on the plug-in studs up and downstream of the outlet openings 57h, 58g and the air in the tool holders 4 is able to flow out at openings in particular at the front ends of the tool holders 4 when the arrangement is upright or vice versa if the tool holders 4 are arranged suspended (FIGS. 7 and 8). If the plug-in studs 85 are fitted with sealing rings, by-pass conduits 57i, 58i should be provided which terminate the supply conduits 57, 58 in the area, particularly the base area, of the plug-in studs 85 radially to the outside and outside the associated pair of sealing rings. When the water supply has been turned off after the water level 35 has been reached and when the heated water reaches a temperature of approx. 40° C., which is determined by a thermometer which is not shown, the solenoid valve 45a or 45b is opened, compressed air being simultaneously blown through the supply lines 57a–57f into the cavities accommodating the mechanical drive elements and the fluid lines of the tool holders 4 and these cavities being blown through and drained. This can be done with cold compressed air or with hot compressed air, heated by the air heater 46. The compressed air heater 46 can be optionally switched on and/or controlled for this purpose. The compressed air draining the cavities is also "barrier air" which prevents the water from penetrating the cavities. The purpose of the throttles in the compressed air distributors 72 and also 68 is to distribute the compressed air uniformly to all supply lines 57a–57f. A few seconds after the solenoid valve 45a has been opened, the ultrasound transducer or transducers 9 provided is or are energized for a short period for the purpose of ultrasonic cleaning. This application of compressed air is then switched off. The same process is repeated at approx. 65° C.

The above-mentioned application of compressed air to the cavities accommodating the mechanical drive elements is of significance. It leads to a draining of the cavities so that in the subsequent ultrasonic cleaning process there is no cavitation damage to the cavity walls and the surfaces of the drive elements.

The water is then heated again until it boils and/or a temperature that is required for disinfection purposes is reached. In this disinfection process in Treatment step C the tool holders are wetted inside and outside with boiling water and are thus disinfected. This disinfection procedure continues for a predetermined time. The water is then pumped into the holding reservoir 37 by means of the pump 29, to be re-used later for a follow-up cleaning process.

The next process is a drying and maintenance process in Treatment step D. In this phase, by opening the solenoid valve 45b the tool holders 4 are blown through with compressed air heated by the air heater 46, this hot compressed air being supplied to both the supply lines 57a–57f and the supply lines 58a–58f at the same time through the compressed air line branches 41a1 and 41a2. Maintenance then takes place by opening the valves 63 and 66a–66f which causes the care agent, in this case a care spray, to be sprayed under pressure through the supply lines 57a–57f into the cavities of the tool holders 4 which accommodate the mechanical drive elements. After this step, which requires only a short period of time, the above-mentioned valves are closed again and the solenoid valve 45a or 45b is opened again or the solenoid valve 45a is left open, causing hot or cold compressed air to be blown into the cavities accommodating the mechanical drive elements through the supply lines 57a–57f and blowing excess care agent out of the cavities. In a follow-up cleaning process the oil emerging at the front ends of the tool holders is cleaned out by means of water returned to the washing chamber 2 from the reservoir 37 and the addition of a surfactant which is briefly introduced into the water bath by opening the solenoid valve 45e. In the course of this exterior cleaning operation hot or cold compressed air is introduced into the tool holders 4 so that no water can enter, cf. the two hot air supply steps (shown by means of thin continuous lines) in FIG. 9 in the area of Process step D.

When the tool holders 4 are being blown out from the inside the water in the washing container 2 is greatly agitated by the compressed air that is blown in, thereby assisting the cleaning action.

After the follow-up cleaning process the water is pumped off into the outlet 13 by means of the pump 29.

In Treatment step E the still relatively high temperature of the tool holders 4 brings about drying (evaporation) of the water adhering to the tool holders 4 after the liquor has been discharged. By blowing cold air into the washing container 2 after opening the solenoid valve 45c the tool holders 4 are cooled down and the external drying is also assisted.

The tool holders 4 can then be removed and further tool holders inserted and a new treatment cycle can begin.

The solenoid valves 66a–66f ensure a relatively accurate metering of the care agent even in a case in which not all mountings 3 are fitted with tool holders 4. Keeping the solenoid valves 66 which are associated with vacant mountings 3 closed prevents care agent from entering the supply lines 57a–57f and then being blown into the associated tool holder in too large a quantity when the relevant mounting 3 is next occupied. This would not only cause an avoidable loss of care agent but the liquor would also be over-dosed with care agent.

The solenoid valves 66 can be manually or automatically controlled. In the latter case a sensor 101, e.g. a magnetic switch 101, which detects the presence or absence of the carrier unit 75 and emits a signal which causes the associated valve or valves 66 to open only if the carrier unit 75 is present, can be assigned to the washing container 2 preferably on the outer side of the edge wall d2. In this embodiment a switching magnet 102 to operate the magnetic switch is provided on the outside of the plug-in connection part 76b.

What is claimed is:

1. A device for selectively cleaning, disinfecting and maintaining medical or dental instruments each including at least one tool holder and having hollow interiors; comprising (a) a washing container for a rinsing liquid for internally and externally washing said instruments or the at least one tool holder;

(b) a carrier for at least one said instrument being arranged in the washing container;

(c) a source of a pressurized gaseous medium, including a supply line for said pressurized gaseous medium extending from said source to the carrier and terminating in a cavity of the instrument which is connected with the carrier;

(d) an automatic or program-controlled control device for controlling means which opens and closes said supply line; and (e) an ultrasonic cleaning device being operatively associated with the selective cleaning, disinfecting and maintaining device for causing the ultrasonic cleaning device to be switched on and of by said control device, and whereby the control device first connects the supply line and thereafter the ultrasonic cleaning device.

2. A device for selectively cleaning, disinfecting and maintaining medical or dental instruments each including at least one tool holder and having hollow interiors; comprising (a) a washing container for a rinsing liquid for internally and externally washing said instruments or the at least one tool holder;

(b) a carrier for at least one said instrument being arranged in the washing container;

(c) a source of a pressurized gaseous medium including a supply line for said pressurized gaseous medium extending from said source to the carrier and terminating in a cavity of the instrument which is connected with the carrier;

(d) a control device for controlling means which opens and closes the supply line; and (e) an ultrasonic cleaning device actuatable by said control device being operatively associated with the selective cleaning, disinfecting and maintaining device, said supply line including first supply lines extending from the pressurized gaseous medium source to the carrier so as to terminate in the cavity of the at least one tool holder accommodating mechanical drive elements for the instrument and second supply lines terminating in a media conduit of the at least one said tool holder whereby the first and second supply lines are opened before actuation of the ultrasonic cleaning device.

3. A device according to claim 1 or 2, wherein said device comprises heating means for the rinsing liquid.

4. A device according to claim 1 or 2, wherein said rinsing liquid consists of water.

5. A device according to claim 1 or 2, wherein said carrier includes a plug-in coupling into which said instrument or at least one said tool holder is insertable, said supply line passing through said plug-in coupling.

6. A device according to claim 5, wherein a further supply line connected to a compressed air source communicates with said carrier, said further supply line passing through the plug-in coupling and being connected to at least one second cavity constituting a fluid conduit of the instrument upon the instrument being arranged in an inserted position in said plug-in coupling.

7. A device according to claim 5, wherein said carrier includes a plurality of said plug-in couplings, said first and second supply lines corresponding in number to said couplings and each being selectively connected to a common care agent and compressed air supply line.

8. A device according to claim 1 or 2, wherein a second pressure source comprising a pressurized medium container is operatively associated with a care agent supply device for maintaining said instruments.

9. A device as claimed in claim 8, wherein said pressurized medium container comprises a pressurized spray bottle.

10. A device according to claim 1 or 2, comprising a plurality of said carriers.

11. A device according to claim 1 or 2, wherein said carrier is detachably fastened in a lower region of the washing container to provide for an upright arrangement of the at least one tool holder, or in an upper region of the washing container for a suspended arrangement of the at least one tool holder.

12. A device as claimed in claim 1 or 2, wherein said washing container is selectively connectable to a supply source for said rinsing liquid and to an outlet for said liquid.

* * * * *